United States Patent [19]

Maslak

[11] 4,140,022

[45] Feb. 20, 1979

[54] ACOUSTIC IMAGING APPARATUS

[75] Inventor: Samuel H. Maslak, Palo Alto, Calif.

[73] Assignee: Hewlett-Packard Company, Palo Alto, Calif.

[21] Appl. No.: 862,454

[22] Filed: Dec. 20, 1977

[51] Int. Cl.$^2$ .................................... G01N 29/04
[52] U.S. Cl. .................................... 73/626; 340/1 R; 340/6 R
[58] Field of Search .................... 73/626, 625, 612; 340/1 R, 3 R, 5 MP, 6 R; 128/2 V, 2.05 Z

[56] References Cited

U.S. PATENT DOCUMENTS

| 3,918,024 | 11/1975 | Macovsi | 73/626 X |
|---|---|---|---|
| 3,938,502 | 2/1976 | Bom | 73/626 X |
| 4,005,382 | 1/1977 | Beaver | 340/1 R |
| 4,012,952 | 3/1977 | Dory | 73/626 X |
| 4,084,582 | 4/1978 | Nigam | 128/2 V |

OTHER PUBLICATIONS

B. S. McCartney, An Improved Electronic Sector-Scanning Sonar Receiver, Journal Brit. I.R.E., Dec. 1961, pp. 481-488, 340-346 R.

Primary Examiner—Richard C. Queisser
Assistant Examiner—John P. Beauchamp
Attorney, Agent, or Firm—Donald N. Timbie

[57] ABSTRACT

An array of transducers is provided for transmitting pulses of ultrasonic pressure waves into a body and translating reflections received into corresponding pulses of electrical waves. Phase changing means, which may preferably include heterodyning means, are connected between each transducer and selected taps on one delay line. The taps are just close enough together to provide reasonable overlap of the pulses of electrical waves at the summing point at one end of the delay line. Focussing is attained by adjusting the phases of the waves applied to each tap so that the cycles of carrier wave within the overlapped portion of the pulses at the summing point have reasonable phase coherence.

36 Claims, 15 Drawing Figures

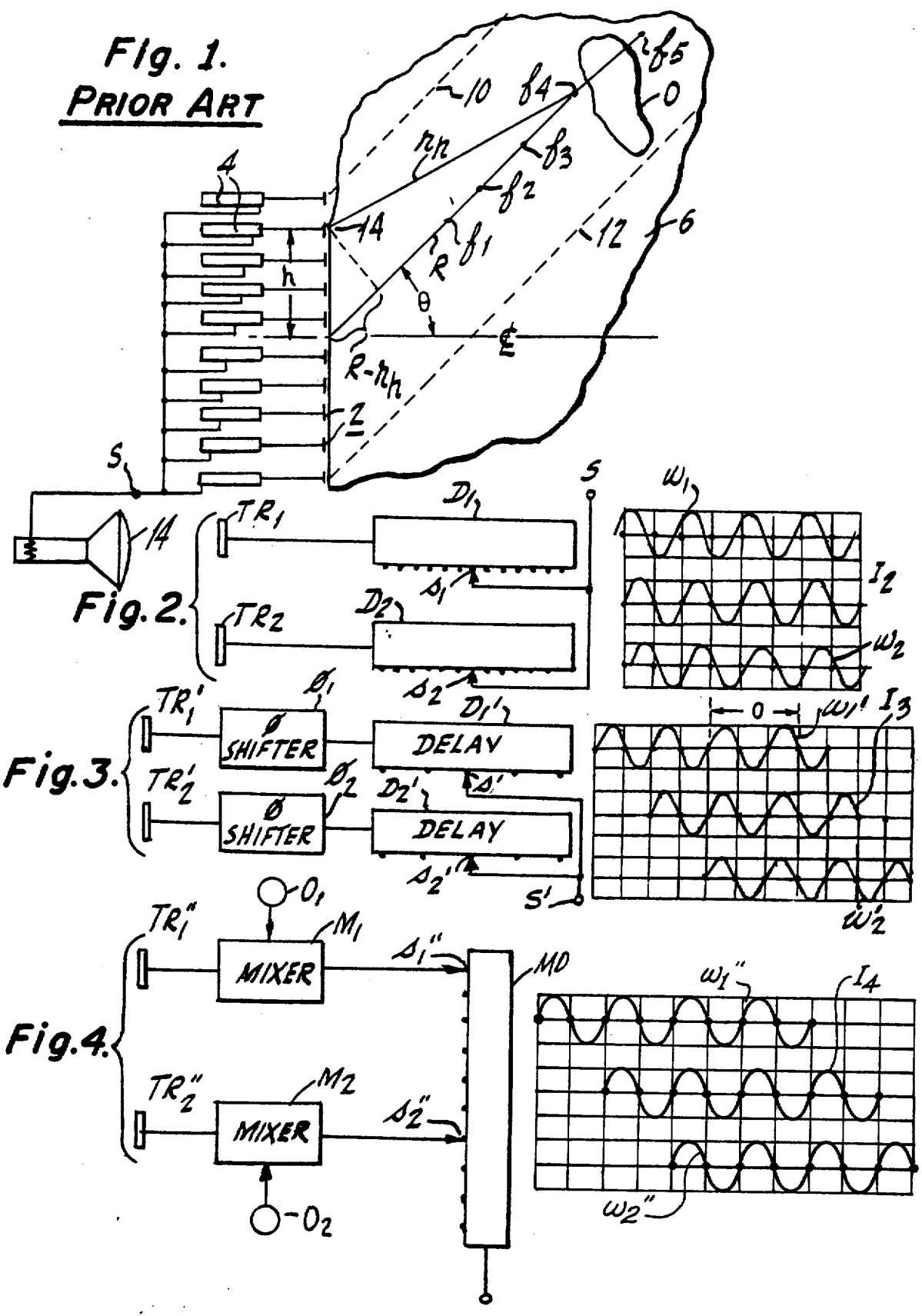

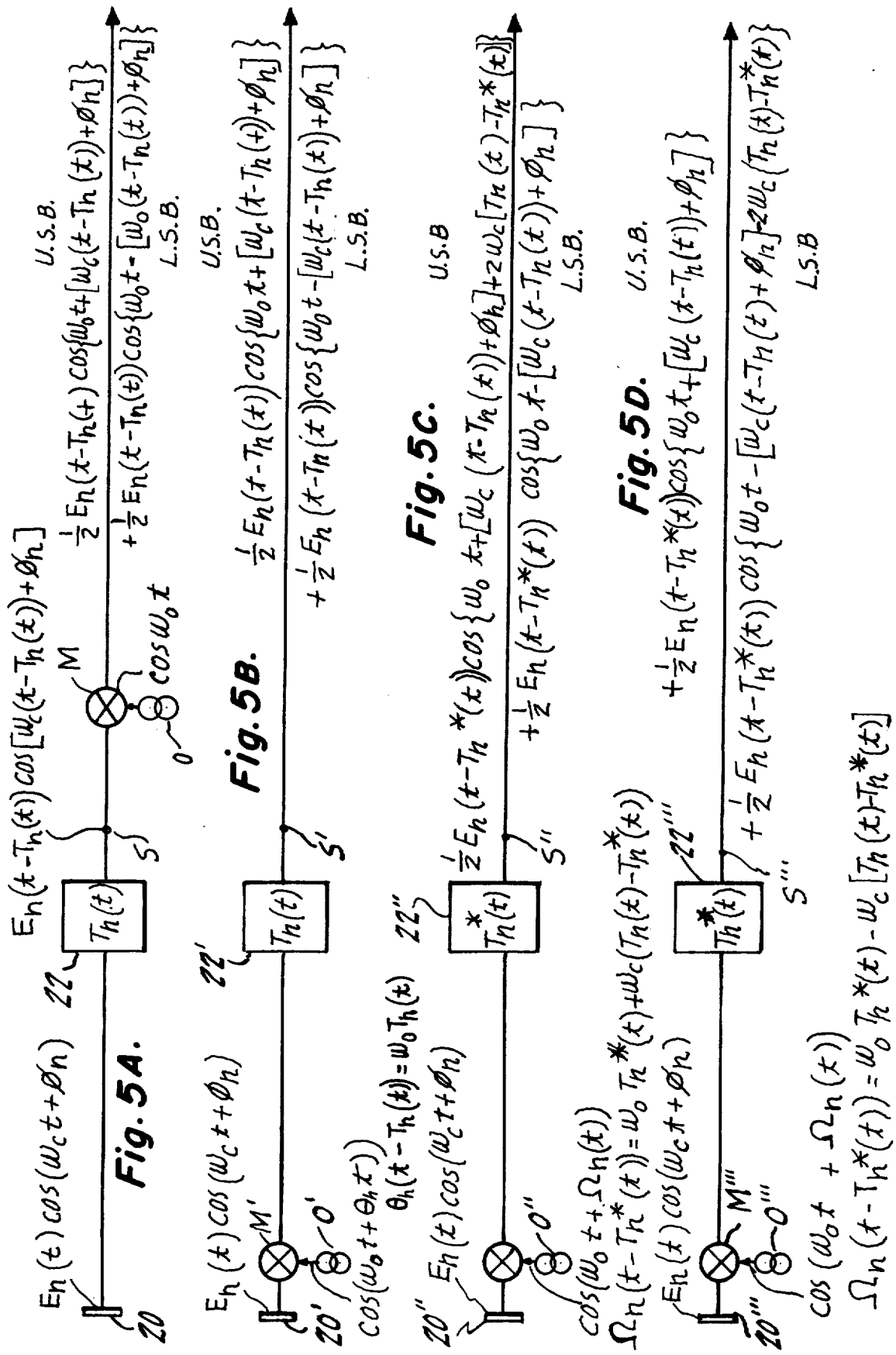

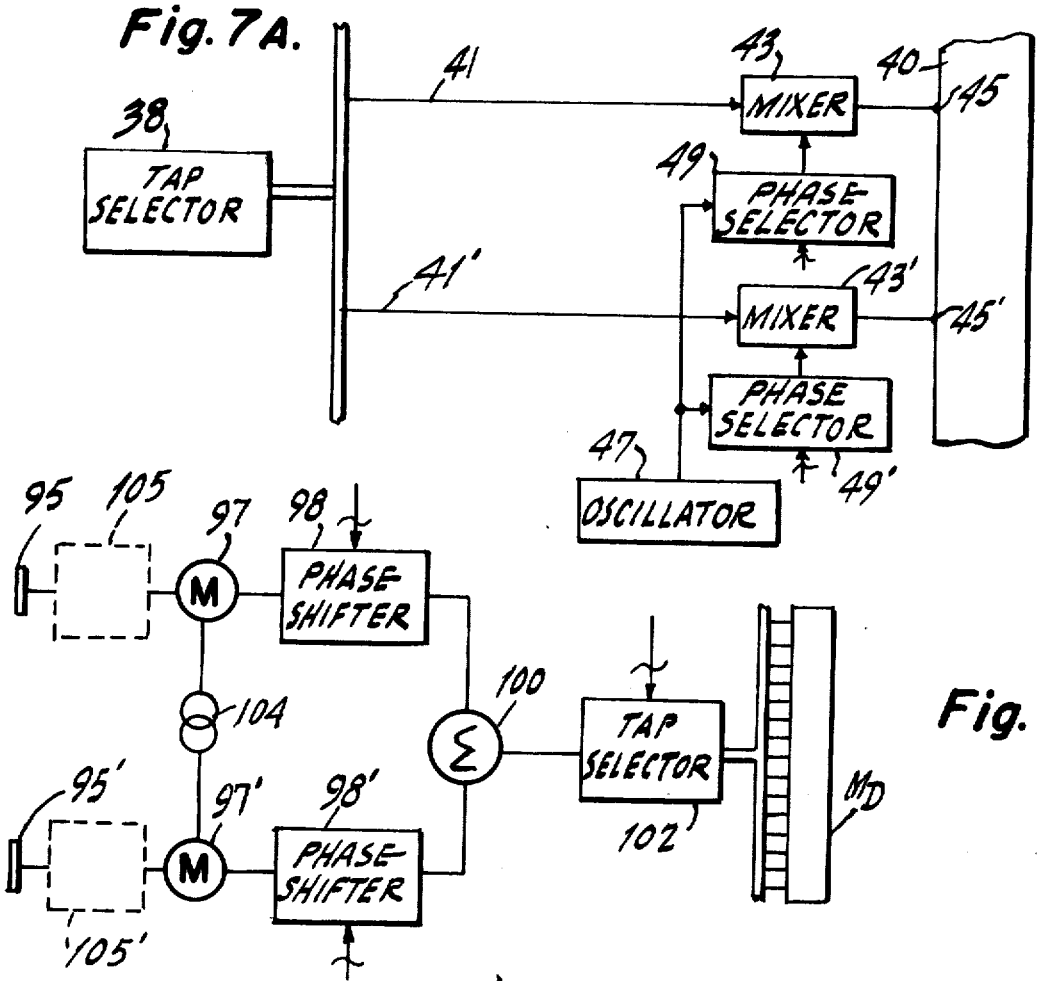
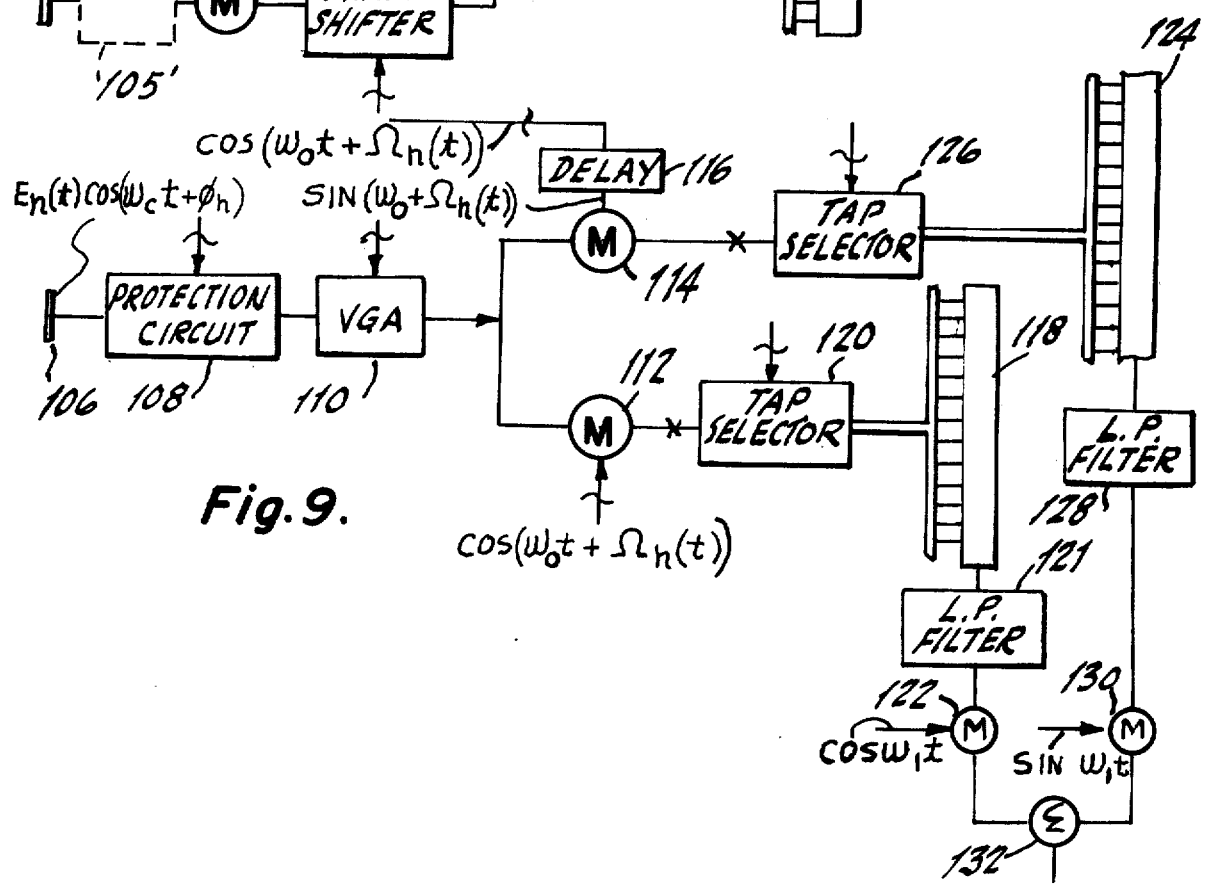

ACOUSTIC IMAGING APPARATUS

BACKGROUND OF THE INVENTION

Much attention has been given in recent years to the development of ultrasonic systems for producing real time images of internal portions of the human body. In one system, an array of transducers for converting short pulses of electrical alternating current carrier waves into corresponding pressure waves is placed in contact with the body. By choosing the relative times of application of the pulses of electrical carrier waves to the transducers, the pressure waves for each pulse can be formed into a beam extending in any desired direction, and the beam direction can be changed so as to effectively scan a sector. As the pulses of pressure waves pass through the body, a portion of their energy is reflected whenever they encounter tissue having a different acoustic characteristic. An array of receiving transducers is provided for converting the reflected pressure waves into corresponding electrical waves.

Precise focussing of the array of receiving elements at a given point requires that all of the few cycles of the alternating current waves derived by each of the transducers from a pulse of pressure waves reflected from that point be superimposed in time synchrony at a summing point so that the pulses are perfectly aligned. This produces a strong signal whereas reflections of pressure waves from other points produce weak signals because the corresponding electrical waves arrive at the summing point with random phase relationships. The distances between any desired focal point and the various receiving transducers being different, the reflections arrive at the transducers at different times. It is therefore necessary in order to achieve precise focussing to introduce compensating delays between each transducer and the summing point so that the total time between reflections of a pressure wave at the focal point and the arrival of the corresponding electrical wave at the summing point is the same regardless of which transducer is involved. The compensating delays may be varied so that the focal point is dynamically scanned from minimum to maximum range along each direction of the transmitted pulses.

In some present equipment, the variations in compensating delays are achieved by changing taps on delay lines. The taps cannot be more than a small fraction of the period of a carrier wave apart if the cycles of the carrier wave are to arrive at the summing point nearly in phase. Inasmuch as the total change in compensating delay for some transducers as they are focussed from minimum to maximum range and from minimum to maximum sector angle is equal to many periods of the carrier wave, the number of taps required is large. At the carrier frequencies employed, only the relatively expensive electrical delay line can be used because of bandwidth considerations, and the provision of a large number of taps on this type of line is a significant portion of the cost of the entire instrument.

Of equal significance is the fact that, unless expensive tap changing switches are used, the switching transients cause a significant amount of noise in the signals arriving at the summing point and therefore in the image produced from them.

The problems of cost and transient noise just referred to increase in severity when the carrier frequency is increased to obtain better definition, the aperture of the array is increased to obtain better focussing, or the minimum range is decreased so as to permit the examination of infants.

BRIEF DESCRIPTION OF THE INVENTION

This invention is especially advantageous when focussing within the near field. Instead of dynamically focussing an array of transducers from minimum to maximum range along each of a plurality of directions by varying their respective compensating delays with changes in connection from one closely spaced delay line tap to another, dynamic focussing is effected in accordance with this invention by changing the phase of AC waves derived from each transducer in such manner that the waves related to each focal point arrive at the summing point with reasonable phase coherence. Inasmuch as the delay line taps are not relied on for producing phase coherence, it is only necessary that they be close enough to provide reasonable overlap at the summing point of the pulses of AC waves derived from the various transducers. Thus, instead of being spaced by a small fraction of the period of an AC wave, the taps can be spaced much farther apart. A spacing corresponding to a delay approximately equal to half the duration of a pulse has been found advantageous. Furthermore, only one or at the most a few tap settings will be required for any transducer while scanning from minimum to maximum range so that the occurrence of tap switching transients are either of no consequence or have very little effect.

The phase changing may be accomplished by phase shifters inserted at some point between each transducer and the summing point, but in accordance with a preferred aspect of the invention, the phase changing is more simply and less expensively effected by respectively heterodyning the carrier waves from each transducer with different phases of an oscillator output that are selected so as to focus the array at one point and changing the phases selected in order to focus the array at successive points along a given direction. The intermediate frequency waves thus derived from each transducer are applied to one of the coarsely spaced taps on a delay line system that have delays nearest to that required for precisely focussing that transducer. With a heterodyning system, the oscillator and the phase selecting means can be digital and therefore less expensive and less noisy than analog oscillators and phase selectors.

By selection of the frequency of the local oscillator, one of the intermediate frequency sidebands of the mixer outputs can be low enough in frequency to permit the use of cheaper electrical delay lines, or it can be made high enough in frequency to permit the use of surface acoustic delay lines that cost must less than an electrical delay line. With respect to cost mush less than an electrical delay line. With respect to the surface acoustic wave delay line, the use of more widely spaced taps in accordance with this invention simplifies design problems because there are fewer taps to cause troublesome reflections. In either case, the phase angle of each local oscillator must include, for reasons that will be explained, a component that compensates for the fact that the delay provided by the coarsely tapped delay line is not that required for precise focussing as well as a component that takes into account the fact that the heterodyning is done ahead of the delay lines.

Another advantage of heterodyning, aside from making it possible to use different types of delay lines, is that if a different carrier frequency is to be used it is only necessary to change the oscillator frequency.

Many systems for utilizing heterodyning in accordance with the invention are possible, each with its own advantages. In some, double heterodyning and/or incremental delay lines may be used. In others, the output of each transducer may be heterodyned with quadrature phases of the oscillator output before being applied to separate delay lines. Whatever the arrangement, the preferred utilization of the invention involves heterodyning the outputs of each transducer prior to the delay lines, controlling the phase of the intermediate frequency waves produced by the heterodyning, and applying the intermediate frequency waves derived from each transducer to only one or at the most a few coarsely spaced taps on a delay line during the focal scansion along each direction.

BRIEF DESCRIPTION OF THE DRAWINGS

FIG. 1 illustrates an ultrasonic system of the prior art;

FIG. 2 illustrates dynamic focussing of the prior art;

FIG. 3 illustrates dynamic focussing by use of phase shifters;

FIG. 4 illustrates dynamic focussing by heterodyning;

FIG. 5A shows a transducer channel of the prior art;

FIG. 5B shows a channel of the invention having an ideal delay;

FIGS. 5C and 5D show channels of the invention having imprecise delays;

FIG. 7A shows an arrangement for using an acoustic delay line in FIG. 7;

FIG. 8 illustrates a portion of an ultrasound system employing heterodyning and wherein the phase of the intermediate frequency wave is changed by phase shifters;

FIG. 9 illustrates an ultrasonic system in which phase quadrature techniques are used;

GENERAL CONSIDERATIONS

Figure 6:
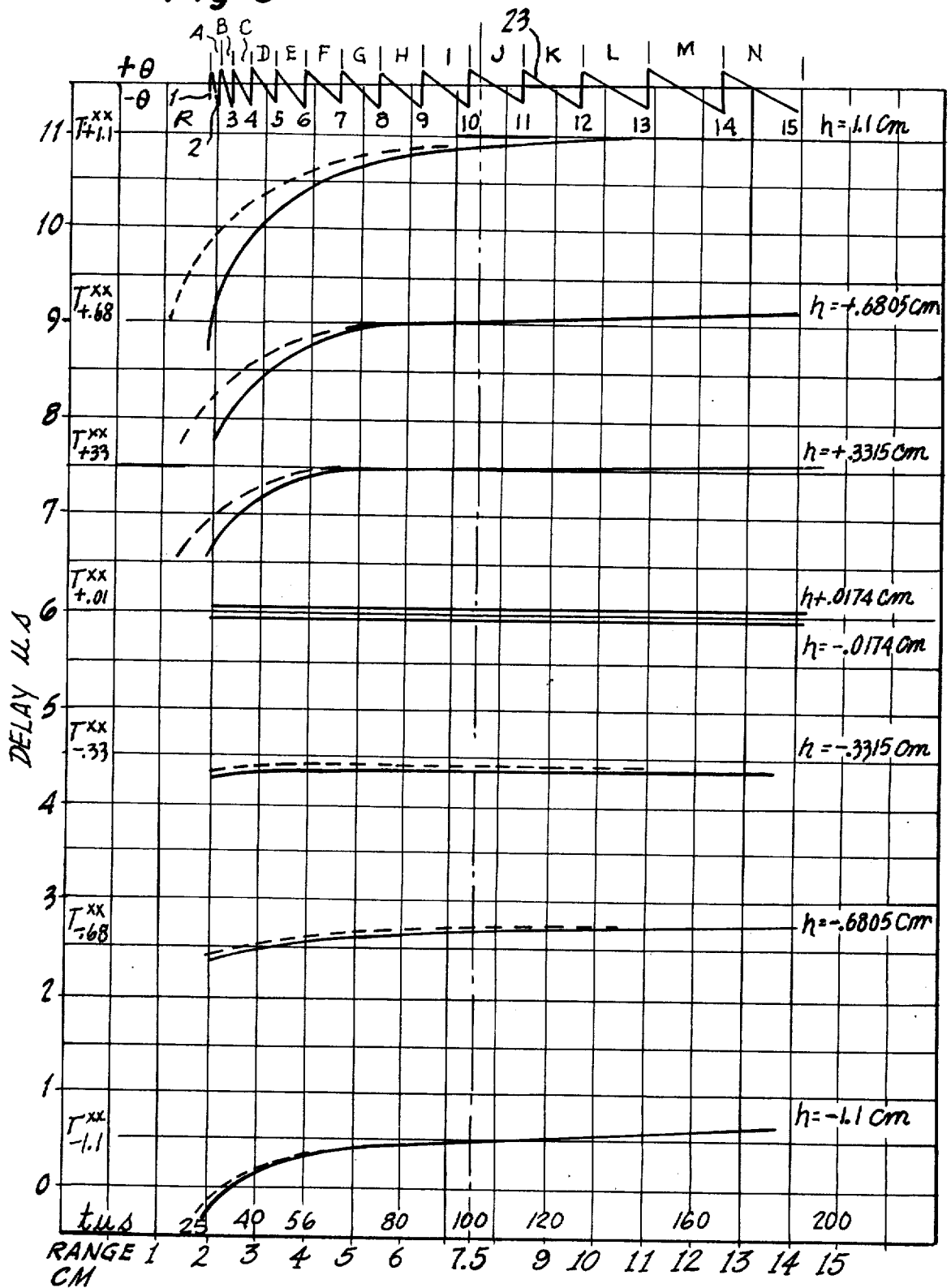
FIG. 6 includes graphs showing the change in delay with time of various transducers as they are focussed along a direction of +45° with the center line of an array.

For purposes of discussion of the general factors involved, consider the ultrasonic system of the prior art shown in FIG. 1. It is comprised of a planar array 2 of transducers that can be used for transmitting acoustic pulses as well as receiving them. A group 4 of delay lines is provided, each having one end connected to a different transducer and a tap connected to a summing point S. The array 2 is shown in contact with a body 6 containing an internal organ O that is to be examined. By means not shown, a few cycles of electrical waves having a carrier frequency $w_c$ are applied to the transducers so as to cause them to transmit pulses of ultrasonic waves of the carrier frequency $w_c$ into the body 6. The relative timing with which the transducers of the array 2 are energized determines the direction and the shape of the wavefront of the beam of acoustic energy thus radiated into the body. If, for example, they are successively energized beginning with the bottom transducer of the array 2, the beam may take a direction at an angle $\theta$ with respect to the center line of the array so that most of the acoustic energy would be in the form of a wave with a planar front moving away from the array 2 between dotted lines 10 and 12. Instead of forming a beam of acoustic energy, it would be possible to energize the transducers so as to cause the wave of acoustic energy to have a curved front, but as far as this invention is concerned, the particular manner of transmitting acoustical energy into the body 6 is unimportant.

In the case illustrated, where a pulse of acoustic energy is transmitted into the body 6 at an angle $\theta$, the receiving array 2 is focussed successively at points $f_1$, $f_2$, $f_3$ and $f_4$, etc., until a maximum range is reached. Then another pulse is transmitted in a slightly different direction and the array is progressively focussed along this new direction. The process is repeated until a desired sector is scanned. When the reflected pulses of acoustic carrier waves reach the transducers, they produce corresponding pulses of electrical carrier waves that are added together at the summing point S after each has been suitably delayed by one of the delay lines 4. The voltage at the summing point S is used to modulate the intensity of the electron beam of a cathode ray tube 14. The beam of the cathode ray tube is deflected so as to follow radial paths corresponding to the different directions scanned by the focal point of the array 2.

Perfect focussing requires that all the carrier wave cycles of the pulses of electrical waves from all transducers arrive at the summing point precisely in phase. The delay, $T_h(t)$, required for perfect focussing of each transducer of a planar array may be defined as that delay which produces an output $X(t-T_h(t))$ when a signal $X(t)$ is applied to its input and may be expressed as follows:

$$T_h(t) = T_o + \frac{(t - T_o)}{2} - \sqrt{\frac{(t - T_o)^2}{4} + \frac{h^2}{c^2} - \frac{(t - T_o) h \sin \theta}{c}} \tag{1}$$

wherein t is the time following the transmission of a pulse from the center of the array, h is the distance of the transducer from the center line of the array, c is the average velocity of the acoustic wave in the body being examined, and $\theta$ is the angle between the center line of the array and the radial line from the center of the array to the focal point. $T_o$ is a fixed delay that is included in each transducer channel so as to prevent the ideal delay, $T_h(t)$, as determined by equation (1) from ever becoming negative.

In prior art arrangements, such as illustrated in FIG. 1, the ideal delay, $T_h(t)$, can be reasonably approximated if the delay line taps are close enough together. For example, if it is decided to keep the cycles of a carrier frequency of 2.5 Mhz within $+22.5°$ of the phase required for perfect focussing, the taps would have to be spaced 50 ns apart, a spacing that would be very expensive.

CONCEPT OF THE INVENTION

Reference is made to FIGS. 2, 3 and 4 for an illustration of some of the advantages derived from the use of certain aspects of the invention.

FIG. 2 shows a system of the prior art, such as already discussed in connection with FIG. 1, wherein transducers $TR_1$ and $TR_2$ are respectively connected to the ends of delay lines $D_1$ and $D_2$. The taps on the delay lines are a fraction of a carrier wavelength apart. If the tap switches $s_1$ and $s_2$ for the delay lines $D_1$ and $D_2$ happen to be connected to taps providing ideal delays, all the cycles of alternating current contained within the pulses provided by the transducers $TR_1$ and $TR_2$ will arrive at the summing point S precisely in phase, as indicated by the wave $I_2$. It is more likely, however, that the switches $s_1$ and $s_2$ will not provide the ideal delays but ones that are a small fraction of a cycle less or a small fraction of a cycle more than the ideal delay so as to produce waves such as $W_1$ and $W_2$ that are close enough in phase to be added effectively. It is noted that as a result of securing adequate phase coherence by adjusting the delays of the AC waves provided by the transducers $TR_1$ and $TR_2$, the pulse overlap of $W_1$ and $W_2$ is nearly 100%.

FIG. 3 illustrates the application of one aspect of this invention, namely, the use of phase shifting means in combination with coarsely tapped delay lines to achieve the phase coherence required for focussing. In this case, phase shifters $\phi_1$ and $\phi_2$ are inserted between transducers $TR_1'$ and $TR_2'$ and their respective delay lines $D_1'$ and $D_2'$. The taps on these delay lines are spaced as far apart as pulse overlap consideration permit so that except in rare instances they are incapable of providing adequate phase coherence of the cycles of the carrier wave at the summing point. If, for example, a pulse with an ideal delay is indicated at $I_3$, the switch $s_1'$ can be set to provide less delay than the switch $s_2'$ so that the respective pulses $W_1'$ and $W_2'$ arrive at the summing point S' as indicated. However, if there is sufficient overlap as indicated at O, and if the phases of the carrier waves are suitably adjusted by the phase shifters $\phi_1$ and $\phi_2$, the cycles of carrier waves within the overlap can add up to a useful signal.

FIG. 4 illustrates the use of heterodyning to achieve focussing in accordance with a preferred aspect of the invention. The transducers $TR_1''$ and $TR_2''$ are respectively connected to one set of inputs of mixers $M_1$ and $M_2$, and oscillators $O_1$ and $O_2$ are respectively connected to the other set of inputs. The output of the mixer $M_1$ is connected by a tap switch $s_1''$ to one input tap on a master delay line MD, and the output of the mixer $M_2$ is connected by a tap switch $s_2''$ to another input tap on the master delay line MD. The taps are spaced far apart, as in FIG. 3, so as to be generally incapable of providing ideal delays. Thus, if an IF wave with an ideal delay arrives at the summing point S'' as indicated at $I_4$, the pulses of intermediate frequency waves from the mixers $M_1$ and $M_2$ may arrive at the summing point S'' at different times, as indicated at $W_1''$ and $W_2''$.

In accordance with a preferred embodiment of this invention, the phase coherence of the intermediate frequency waves in the overlapped portion of the pulses is secured by respectively adjusting the phase angles of the outputs of the oscillators $O_1$ and $O_2$ to angles $\Omega_1$ and $\Omega_2$ that are determined in a manner to be described.

DETERMINATION OF THE PHASE ANGLE

FIG. 5A shows a transducer channel in which the electrical signal $$E_h(t) \cos(w_c t + \phi_h). \qquad (2)$$

from a transducer 20 is delayed by a delay line 22 by the ideal amount $T_h(t)$ so as to arrive at a summing point S in the form $$E_h(t - T_h(t)) \cos[w_c(t - T_h(t)) + \phi_h]. \qquad (3)$$

This signal is in phase with the signals provided by all the other transducer channels, not shown, if their delay lines have ideal delays calculated from equation (1) and if the signals are caused by reflection of a transmitted pulse from a target located at range $c(t - T_o)/2$ and at angle $\theta_h$. The phase angle $\phi_h$ is the angle between acoustic carrier waves transmitted from the center of the array and the reflected acoustic waves arriving at a transducer. It is different for each transducer owing to the fact that the waves have to travel different distances, but this difference is precisely compensated by the different values of $T_h(t)$.

Although it would not ordinarily be done, the signals from all the channels that are summed at the point S are applied for purposes of explanation to a mixer M wherein they are heterodyned with the output $\cos w_o t$ of an oscillator O. It is possible to select the oscillator frequency so that all the signal information is included in each sideband. If the signal at the output of the mixer M due to the transducer channel shown could be separated from the others, it would have an upper sideband expressed by $$U.S.B. = \tfrac{1}{2} E_h(t - T_h(t)) \cos\{w_o t + [w_c(t - T_h(t)) + \phi_h]\} \qquad (4)$$

and a lower sideband expressed by $$L.S.B. = \tfrac{1}{2} E_h(t - T_h(t)) \cos\{w_o t - [w_c(t - T_h(t)) + \phi_h]\}. \qquad (5)$$

Heterodyning in this way does not disturb phase coherence so that the upper sidebands of all channels will all have the phase determined by equation (4) and the lower sidebands will have the phase determined by the equation (5).

As previously pointed out, certain embodiments of the invention may require the waves from the transducers to be heterodyned before the delay lines. If this can be done so as to produce either an upper or lower sideband having the same phase at the output of the delay lines as the upper or lower sidebands of FIG. 5A, the necessary phase coherence can be attained.

Accordingly, consider FIG. 5B which shows a transducer channel incorporating one aspect of this invention in which components similar to those of FIG. 5A are designated by the same numbers or letters primed. The signal provided by the transducer 20' is the same as before, i.e., in accordance with expression (2). The essential difference is that the mixer M' is inserted between the transducer 20' and the delay line 22'. In this case, the oscillator O' is assumed to have a phase angle $\theta_h(t)$, whereas the oscillator O in FIG. 5A had a phase angle of zero. In calculating phase angles, whole numbers of cycles are ignored, modulo $2\pi$ radians, so that the fraction of a cycle left over determines the phase. In the following, equality between phase angles should be interpreted as equality modulo $2\pi$ radians. If, in accordance with this invention, $$\theta_h(t - T_h(t)) = w_o T_h(t), \qquad (6)$$

the upper and lower sidebands at the summing point S' of FIG. 5B are respectively the same as the upper and lower sidebands at the output of the mixer M of FIG. 5A and therefore the same as respectively represented by the expressions (4) and (5). By using the phase angle $\theta_h(t)$ for channel h, for each channel, the upper sidebands of all channels will be in phase at the summing point S' as will be the lower sidebands. A practical advantage of this invention is that each sideband contains all the signal information so that the delay lines need pass only one of them.

However, if in accordance with one aspect of this invention the taps on a delay line provide a delay $T_h^*(t)$ that differs significantly from the ideal delay $T_h(t)$, the situation is as indicated in FIGS. 5C and 5D. The components of FIG. 5C corresponding to those of FIG. 5A are indicated by the same letter or number with a double prime, and the components of FIG. 5D corresponding to those of FIG. 5A are designated by the same numbers or letters with a triple prime. In each figure, the transducer signal $E_h(t)\cos(w_c t + \phi_h)$ is heterodyned with an oscillator output having the form $\cos(w_o t + \Omega_h(t))$, but the definition of the phase angle $\Omega_h(t)$ is different.

In FIG. 5C, $\Omega_h(t)$ is defined in accordance with this invention so as to satisfy the expression $$\Omega_h(t-T_h^*(t)) = w_o T_h^*(t) + w_c[T_h(t) - T_h^*(t)]. \tag{7}$$

As indicated in the drawing, the phase of the lower sideband at the summing point S'' is the same as the phase of the lower sidebands of FIGS. 5A and 5B described by the expression (5). Therefore, the lower sidebands of all transducer channels like the one shown in FIG. 5C will be precisely in phase at the summing point S''. Note, however, that the expression for the upper sideband in FIG. 5C, $$\tfrac{1}{2} E_h(t-T_h^*(t)) \cos\{w_o t + [w_c(t-T_h(t)) + \phi_h] + 2w_c[T_h(t) - T_h^*(t)]\}, \tag{8}$$

differs from the expression (4) for the upper sidebands of FIGS. 5A and 5B by inclusion of the phase term $+2w_c[T_h(t) - T_h^*(t)]$. Therefore, the upper sidebands of the channels at the summing point S'' will not be in place, so only the lower sidebands can be used.

The envelope $\tfrac{1}{2} E_h(t-T_h^*(t))$ of the sidebands in FIG. 5C differs from the envelope $\tfrac{1}{2} E_h(t-T_h(t))$ of the sidebands in FIGS. 5A and 5B on account of a time shift of $[T_h(t) - T_h^*(t)]$. This difference in envelope time delay does not, in itself, affect the phase coherence among the transducer channels; rather, it affects the amount of pulse overlap.

In FIG. 5D, $\Omega_h(t)$ is defined in accordance with this invention so as to satisfy the expression $$\Omega_h(t-T_h^*(t)) = w_o T_h^*(t) - w_c[T_h(t) - T_h^*(t)], \tag{9}$$

the difference from equation (7) being the minus sign instead of a plus sign between the two terms on the right side of the equation. As indicated in the drawing, the phase of the upper sideband is the same as the phase of the upper sidebands of FIGS. 5A and 5B described by the expression (4). Therefore, the upper sidebands of all transducer channels like the one in FIG. 5D will be precisely in phase at the summing point S'''. Note, however, that the expression for the lower sideband in FIG. 5D, $$\tfrac{1}{2} E_h(t-T_h^*(t)) \cos\{w_o t - [w_c(t-T_h(t)) + \phi_h] - 2w_c[T_h(t) - T_h^*(t)]\}, \tag{10}$$

differs from the expression (5) for the lower sidebands of FIGS. 5A and 5B by inclusion of the phase term $-2w_c[T_h(t)-T_h^*(t)]$. Therefore, the lower sidebands of the channels at the summing point S''' are not in phase, so only the upper sidebands can be used.

Inasmuch as the phase coherence at the summing point of the waves of the appropriate sideband of the intermediate frequency no longer depends solely on the delays provided at the taps to which the transducers are connected, the taps can be selected for each transducer at the beginning of the focal scanning along each radial direction and remain unchanged so as to provide a delay $T_h^{**}$ until the start of the scanning of the next radial direction. In this case, the variable $T_h^*(t)$ in equations (7) and (9) becomes a constant $T_h^{}$ so that the equations (7) and (9) can be respectively expressed as $$\Omega_h(t-T_h^{}) = w_o T_h^{} + w_c[T_h(t) - T_h^{}] \tag{11}$$

and $$\Omega_h(t-T_h^{}) = w_o T_h^{} - w_c[T_h(t) - T_h^{**}]. \tag{12}$$

By substituting the expression $t+T_h^{}$ for the free variable t, we see that equations (11) and (12) can be made to respectively define the phase angle in explicit rather than implicit form as $$\Omega_h(t) = w_o T_h^{} + w_c[T_h(t + T_h^{**}] \tag{13}$$

and $$\Omega_h(t) = w_o T_h^{} - w_c[T_h(t + T_h^{}]. \tag{14}$$

If equation (13) is selected for the calculation of $\Omega_h(t)$, the lower sideband must be used, and if equation (14) is used, the upper sideband must be used.

PRACTICAL ILLUSTRATION

From equation (13), it can be seen that the phase angle $\Omega_h$ to be used at any time t is comprised of a fixed component, intermediate frequency by its passage through the delay provided at the tap to which the transducer is coupled, and a variable component, $w_c[T_h(t+T_h^{}) - T_h^{}]$, which provides a phase angle that changes with time so as to make the cycles of the intermediate frequency waves related to successive focal points arrive at the summing point in phase with each other.

By way of illustration, consider the solid line graphs of FIG. 6 which represent the variations in the ideal delay $T_h(t)$ with time that is required in accordance with equation (1) to focus each of eight transducers that are symmetrically located about the center line of an array from a range of 1.4 cm to a range of 15.0 cm along a direction $\theta = +45°$. The distance h from the center of the array of each transducer is set forth at the right end of its graph. The transducers may be connected during each focal scansion from minimum to maximum range to a tap having the delay $T_h^{}$ closest to the ideal $T_h(t)$ for some range such as 7.5 cm. If the taps are located at each half us, the transducers at h = +1.1, +0.68, +0.33, +0.02, −0.02, −0.33, −0.68 and −1.1 cms will be respectively connected to taps having delays, $T_h^{}$, of 11, 9, 7.5, 6, 6, 4.5, 2.5 and 0.5 us. The value of the fixed term $w_o T_h^{}$ of equation (13) for each transducer is then obtained by multiplying values of $T_h^{}$ by the oscillator angular frequency $w_o$.

The dotted line graphs represent the variations $T_h(t+T_h^{})$ and are formed by moving the solid line graphs to the left by an amount of time equal to the delay $T_h^{}$ for each transducer. The total number of radians for $w_c T_h(t+T_h^{})$ at any time t is determined by multiplying the corresponding delay of the dotted curve for that time by $w_c$. Note that this number of radians occurs $T_h^{}$ us earlier than would be the case if the solid line curves were used. The reason for this time shift is that it takes $T_h^{}$ us for any change on the input of the delay line system to reach the summing point and the changes must reach the summing point at the same time. The value of $w_c T_h^{}$ is then calculated and subtracted from the value obtained for $w_c T_h(t+T_h^{})$, and this result is added to $w_o T_h^{}$. The number of radians by which the result differs from the nearest integral multiple of 2 is the value of $\Omega_h(t)$.

CONTROL OF THE PHASE ANGLES $\Omega_h$

Changing the phase angles $\Omega_h$ continuously so as to provide perfect phase coherence of the cycles of intermediate frequency waves for all ranges would be very expensive, but a phase coherence that is within +22.5° has been found satisfactory. Starting at some initial time, the phase angles for the transducer channels can be set at values that are respectively 22.5° greater than the values required for perfect focussing at that time. These values are maintained until times when they are 22.5° less than the values required for perfect focussing. At these times, the phase angles are increased by 45° so as to once again be 22.5° greater than the phase angle required for focussing. The changes occur whenever the delays $T_h(t+T_h^{**})$ represented by the dotted graphs of FIG. 6 change by one-eighth of the period of the carrier frequency $w_c$. An even less expensive method is to arbitrarily change the phase angles for all transducer channels at relatively fewer ranges such as $R_1$-$R_{15}$ of the graph 23 of FIG. 6 to values that are the closest 45° multiple to the phase required for perfect focussing at the mid points of the respectively successive focal zones Z-N. The ranges $R_1$-$R_{15}$ might be those at which 45° changes would be required to maintain the phase error within +22.5° for some transducer between the center and end of the array, in which case the phase error for this transducer would vary between a +22.5° and a −22.5°. Greater phase errors would occur in the channels for transducers farther from the center of the array and smaller phase errors would occur in the channels for transducers closer to the center of the array.

DESCRIPTION OF A PREFERRED EMBODIMENT

Figure 7:
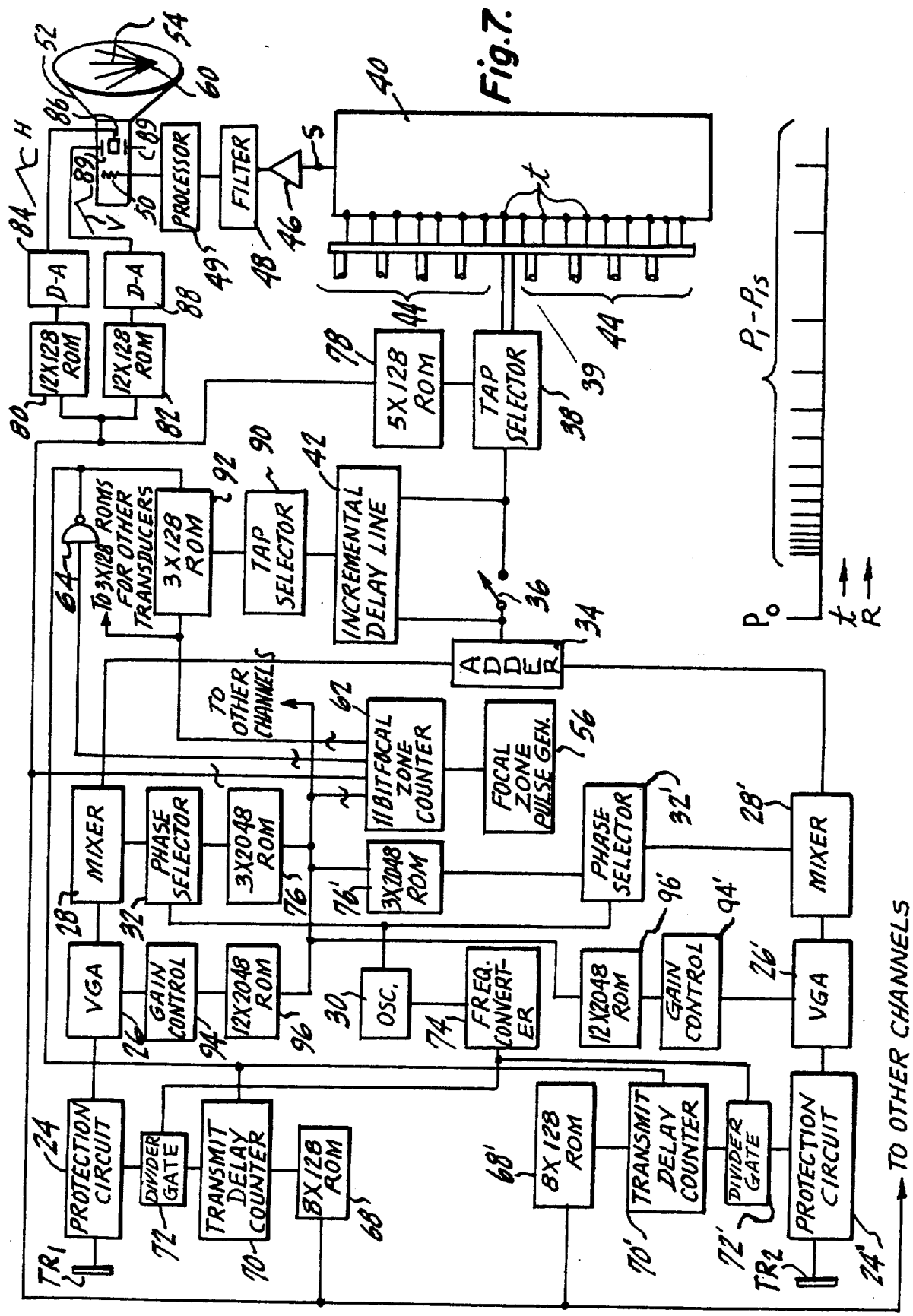
FIG. 7 illustrates a portion of an ultrasonic system using heterodyning for changing the carrier frequency and attaining phase coherence.

FIG. 7 illustrates an ultrasonic system of this invention wherein the phase of the intermediate frequency waves is changed in 45° steps and the setting of the taps on the master delay line for each transducer is made at the beginning of the focal scansion of each radial direction. Only two adjacent transducer channels are shown, one for a transducer $TR_1$ and one for a transducer $TR_2$, but in practice sixteen or more transducers are generally used. Corresponding components for the channel associated with $TR_2$ are indicated by the same numerals primed.

$TR_1$ converts acoustic pulses of a frequency $w_c$ to corresponding electrical waves that pass through a protection circuit 24 and a variable gain amplifier 26 to a mixer 28 where they are heterodyned with one of eight phases (in 45° increments) produced by an oscillator 30 and selected by a phase selector 32. The eight-phased outputs of the oscillator 30 may be digital, as produced by a Johnson counter, for example, in which case phase selector 32 may be a simple 1 of 8 digital logic data selector. The intermediate frequencies ($w_o$ − $w_c$) and ($w_o + w_c$), produced by the mixer 28, are applied to an adder 34 where they are combined with the intermediate frequencies produced by a similar adjacent channel, such as that associated with the transducer $TR_2$. A switch 36 is connected between the output of the adder 34 and an input of a tap selector 38. When the switch 36 is open, the delay provided by an incremental delay line 42 is inserted between the adder 34 and the tap selector 38. When the switch 36 is closed, the incremental delay line is bypassed. The addition of the intermediate frequencies of adjacent channels in an adder such as 34 reduces the number of tap selectors and does not deteriorate the image because the phase-adjusted intermediate frequency signals of adjacent channels are very nearly alike.

The tap selector 38 selectively connects its input to one of a plurality of conductors in a bus system 39. Each conductor of the bus system is connected to a different tap t on the master delay line 40. Pulses of intermediate frequency supplied by other pairs of transducer channels, not shown, are applied to the inputs of tap selectors like 38, and the outputs of each tap selector are respectively connected to the conductors in the bus system 39 via one of the inputs indicated at 44. Many different tap selectors may connect their respective transducer channel pairs to the same tap on the master delay line, or to different taps, as required. As the pulses enter the delay line at a point determined by the tap selection, they add to the pulses inserted in the line at previous taps, so that all the pulses are combined at the summing point S to provide a video signal. After amplification by an amplifier 46, the appropriate intermediate frequency band of the video signal is selected by a filter 48 before it is applied via a signal processing means 49, which may include a detector, to the intensity control electrode 50 of a cathode ray tube 52. If the phase angles $\Omega_h(t)$ are in accordance with the equation (13), the lower sideband is selected by the filter 48, and if they are in accordance with the equation (14), the upper sideband is selected. It is only necessary that the delay line 40 pass the frequency band selected by the filter. The beam of the cathode ray tube is deflected so as to follow a pattern of radial directions 54 that correspond to the radial directions along which the array of transducers is focussed in the body of the patient being examined.

CONTROL SYSTEM

Control of the various functions performed by the ultrasonic system shown in FIG. 7 may be effected in many ways. In this system, the array of transducers is focussed at each of 16 focal zones along each of 128 radial directions. The heart of the control system is a focal zone pulse generator 56 that produces pulses $P_0$ and $P_1$-$P_{15}$ in repeated sequence so that, after start-up, every sixteenth pulse corresponds to the pulse $P_0$. The pulses $P_1$-$P_{15}$ occur at the corresponding ranges $R_1$-$R_{15}$ of FIG. 6. The large space between the pulse $P_0$ and the first focal zone pulse P₁ represents the range below the minimum for which the system is designed. The pulses P₁-P₁₅ are progressively further apart as would be expected from the previous consideration of the graphs of FIG. 6.

CONTROL OF TRANSMITTED PULSES

The radial direction of a transmitted acoustic pulse is determined by the relative times at which the transducers of the array are energized. The electrical pulses $P_0$-$P_{15}$ from the focal zone generator 56 are applied to a counter 62 that outputs a different digital word in response to each pulse. The first four bits 1, 2, 3 and 4 of each word are applied to a NAND gate 64 that produces an output pulse in response to every sixteenth pulse, i.e., each output pulse is coincident with a pulse $P_0$. This pulse is applied to start the counting of a transmit delay counter 70. If the acoustic pulses are to be transmitted in 128 different directions in sequence, the seven bits (5, 6, 7, 8, 9, 10 and 11) of counter 62 are applied so as to address an 8 × 128 ROM 68 and cause it to output one of 128 combinations of eight bits at the time of each pulse $P_0$. Each combination of eight bits causes the transmit delay control counter 70 to output a pulse at one of 256 different times after a pulse $P_0$. The output pulse from the counter 70 is applied so as to open a divider-gate 72 and permit a few cycles of the correct phase of a carrier wave frequency $w_c$ derived by the divider-gate 72 from the frequency converter 74 to pass to the transducer TR₁ via the protection circuit 24. The purpose of the latter is to prevent these pulses from damaging the receiver channel. The transmission of pulses of carrier waves $w_c$ from the transducer TR₂ is controlled by corresponding components indicated by the same numerals primed. The time of the pulse transmitted by TR₂ will generally be slightly earlier or later than the pulse transmitted by TR₁ as determined by information contained in ROM 68'.

CONTROL OF PHASE SELECTION

The phase angle $\Omega_h(t)$ that is required for the waves of local oscillator frequency in accordance with the invention is controlled in the following way. The digital output of the focal zone counter 62 is applied to the address inputs of a 3 × 2048 bit ROM 76 so as to cause it to output one of eight prestored combinations of 3 bits at the time of each of the pulses $P_0$-$P_{15}$ at each of the 128 sector angles. Each different combination can cause the phase selector 32 to select a different 45° phase of the output of the oscillator 30 and apply it to the mixer 28. The 45° phase selected is that one which is closest to the precise angle required at the median value of $\Omega_h(t)$ as determined from equations (13) or (14) for the focal zone following the pulse. If there are to be 16 focal zones along each of 128 different radial directions, the 2048 different combinations that are required are provided by the ROM 76. The ROM 76' operates in the same way to cause the phase selector 32' to apply the appropriate phases of the output of the oscillator 30 to the mixer 28'.

CONTROL OF MASTER DELAY LINE TAPS

In this particular arrangement, the tap on the master delay line 40 is selected at the time of each pulse $P_0$ and is not changed until the pulse $P_0$ at the start of the next radial line. Seven bits (5, 6, 7, 8, 9, 10 and 11) of counter 62 address a 5 × 128 ROM 78. The five bit output of the ROM causes the tap selector 38 to apply the output of the adder 34 to one of thirty-two taps on the delay line 40 (only seventeen are shown). If the taps are to be those nearest the delay required for a range of 7.5 cm, along a scan angle of +45°, they are those indicated in FIG. 6. Additional ROMs and tap selectors are required for other phase-pairs (not shown). Switch 36 is closed because the incremental delay line 42 is not used in this example.

CONTROL OF CRT DEFLECTION

In order to control the deflection of the beam of the cathode ray tube 52 so that it scans a pattern of 128 different radial lines as schematically indicated at 54, bits 5, 6, 7, 8, 9, 10 and 11 of counter 62 are applied to two 12 × 128 ROMs, 80 and 82, so that they output a twelve bit word at the start of each radial line. The words provided by the ROM 80 determine the slope of the horizontal deflection wave H provided by a D-A ramp generator 84 to a horizontal deflection plate 86, and the words provided by the ROM 82 determine the slope of the vertical deflection wave V provided by a ramp generator 88 to a vertical deflection plate 89.

CONTROL OF THE TAPS ON THE INCREMENTAL DELAY LINE

If the tap on the master delay line 40 is selected at the beginning of the focal scanning of each radial line, i.e., at the time of each pulse $P_0$, and is not changed during the line, the difference between the ideal delay $T_h(t)$ and the actual delay $T_h^{}$ provided by the tap may become so great and the resulting overlap of the pulses so small as to impair the range or angular resolution of the image. Under such circumstances, the taps on the master delay line could be changed during the line by making the ROM 78 have a 5 × 2048 bit memory, and addressing it with all eleven bits from the focal zone counter 62** so that it can make the tap selector change taps as many as sixteen times during the scanning of each radial line. It is contemplated, however, that the taps will not have to be changed often so as to avoid the use of expensive tap selectors required to reduce noise.

Another alternative is to insert the incremental delay line 42 between the adder 34 and the tap selector 38 in accordance with an invention of Richard D. Pering, described in U.S. patent application Ser. No. 718,721, filed on Aug. 30, 1976. The delay between the taps of the incremental delay line 42 is less than or comparable to the differential delay between taps on the master delay line 40, so that selecting an appropriate tap on the incremental line 42 at the beginning of each focal zone will result in the combined delay $T_h^*(t)$ of both lines being more nearly equal to the ideal delay $T_h(t)$. This may be done by controlling a tap selector 90 so as to select one tap on the incremental line 42 with a 2048 × 4 bit ROM 92 that is addressed by the focal zone counter 62. The switch 36 would have to be open but, in an actual equipment, the switch would not be needed, as the incremental line 42 could be programmed to have zero delay. The switch is shown to indicate that the incremental delay line may not be used.

When inserting the incremental delay line 42 as just described, the value of the phase angle $\Omega_h(t)$ will differ from the preceding example. The tap on the master delay line 40 is set by the ROM 78 and the tap selector 38 at the closest delay, $T_{MD}$, below the smallest ideal delay $T_h(t)$ for a particular scan line. If the delay of the incremental line, $T_{ID}(t)$, is set as indicated by the following equation, the actual delay provided by the combination of the two delay lines would equal the ideal delay $T_h(t)$ as given in equation (1).

$$T_{ID}(t) = T_o - T_{MD} + \frac{(t + T_{MD} - T_o)}{2} - \sqrt{\frac{(t + T_{MD} - T_o)^2}{4} + \frac{h^2}{c^2} - \frac{(t + T_{MD} - T_o)h \sin\theta}{c}} \quad (15)$$

With the taps on the incremental delay line coarsely spaced in accordance with an aspect of this invention, the combined delay can only approximate the ideal delay $T_h(t)$. The sum of $T_{ID}$ and $T_{MD}$ is used as $T_h^{**}$ in calculating the phase angle $\Omega_h(t)$ from equations (13) or (14) that would be supplied by the phase selectors 32 and 32'.

CONTROL OF CHANNEL GAIN

As an alternative technique to using an incremental delay line when the range resolution is impaired by the fact that the actual delay $T_h^{**}$ provided by a tap on the master delay line 40 is too different from the ideal delay, $T_h(t)$, the transducer channel can be turned off. This can be done by controlling a gain control 94 for the variable gain amplifier 26 with a 2048 × 12 bit ROM 96 that is addressed by the output of the focal zone counter 62. These components can also be used to increase the gain of the channel as the range increases so as to compensate for the attenuation of the acoustic waves as they pass through the body.

ADAPTATION FOR AN ACOUSTIC LINE

The ultrasonic system of FIG. 7 can be used as shown whether the master delay line 40 is electrical or acoustic, but certain advantages can be derived from incorporating an acoustic line, as shown in FIG. 7A. The tap selector 38 is essentially a multiposition switch that connects its input to one of a number of output leads. One output lead is provided for each tap on the delay line 40. For convenience, only two output leads 41 and 41' are shown. In FIG. 7A, the lead 41 is coupled to one input of a mixer 43, and the output of the mixer 43 is connected to a tap 45 on the delay line 40. The other input of the mixer 43 is connected to a preset phase selector 49 that selects a phase of an oscillator 47. If the center frequency of the delay line 40 is 20 MHz, and the intermediate frequency $(w_o - w_c)/2\pi$ is 2 MHz, the frequency of the oscillator 47 may be 18 MHz. Similarly, the lead 41' is coupled to a tap 45' on the master delay line by a mixer 43' which is supplied with a phase of the output of the oscillator 47 selected by a preset phase selector 49'.

When an electrical delay line is used, the delay between taps can be precisely trimmed to a desired value such as 0.5 us by physically adding sections of delay line, as need be, but with an acoustic line, this is not possible.

The purpose of the preset phase selectors 49 and 49' is to adjust for slight errors in the spacing of the taps 45 and 45' on the acoustic delay line 40. The phase shifts $\Omega_h(t)$ required for focussing may be provided by the first heterodyning in the mixers 28 and 28' in FIG. 7. The phase shifts required for compensating the error in tap spacing may be provided by the phase selectors 49 and 49' or by other means, such as tuned circuits, etc.

By using the circuit configuration of FIG. 7A, it is possible to change from a delay line operating at one frequency to a delay line operating at another frequency without changing any other part of the circuit, so that the ROMs 76 and 76' and their associated phase selectors 32 and 32' continue to operate in exactly the same way and impart the same phase angles $\Omega_h$ to the intermediate frequency waves at the outputs of the mixers 28 and 28'. The frequency $w_1$ of the oscillator 47 is set so as to produce a band of intermediate frequencies at the outputs of the mixers 43 and 43' that falls within the pass band of the delay line 40, and the phase selectors such as 49 and 49' are controlled so as to respectively add to any fixed phase component that may be required for compensation for any error in tap spacing a second fixed phase component $w_1 T_h^{}$, wherein $T_h^{}$ are the delays provided by the taps on master delay line 40 to which the mixers such as 43 and 43' are respectively connected.

In FIG. 7, the means shown for determining the phase of the oscillator frequency to be applied to the mixers and for selecting the taps on the incremental and master delay lines includes separate ROMs in which the necessary digital information has been stored, but as well understood by those skilled in the art, the information could be stored in a memory having fewer bits if this memory is shared. It is also possible to compute the information on a real time basis in a microprocessor. Other scan formats and control techniques could be used in a system incorporating this invention.

In the various calculations, it has been assumed that the transducers lie on a straight line, but if they lie on a differently shaped line, the formula for the ideal delay $T_h(t)$ for a transducer would be different, but the phase required for focussing would still relate $T_h(t)$ and $T_h^{**}$ in the same way as in equations (13) and (14).

PHASE CHANGING MEANS

In the transducer channels of FIG. 7, the means for changing the phase $\Omega_h(t)$ of the waves derived from the transducer and applied to a tap on the delay line is comprised of a mixer, an oscillator, and a phase selector; but the means for changing the phase can include a phase shifter connected in series with each mixer if it is such that an input signal $\cos(w_c t + \phi)$, when shifted by $\Omega(t)$, produces a signal $\cos(w_c t + \phi + \Omega(t))$. By way of illustration, FIG. 8 shows a transducer channel comprised of a transducer 95, a mixer 97, and a phase shifter 98 connected in series to one input of an adder 100, and a similar adjacent channel comprised of a transducer 95', a mixer 97', and a phase shifter 98' connected in series to another input of the adder 100. The output of the adder 100 is selectively connected to a tap on the master delay line $M_D$ by a tap selector 102, and an oscillator 104 provides the same phase of an oscillator frequency $w_o$ to the mixers 97 and 97'. The phase shifter can be digitally controlled in any well-known manner with information like that stored in the ROM 76 of FIG. 7. The phase shifters could alternatively be located between the transducers and the mixers, as indicated by the dotted rectangles 105 and 105'. Although less desirable in many applications, the phase changing means could be comprised of just a phase shifter, but no mixer, as shown in FIG. 3.

QUADRATURE SYSTEM

In discussing the system of FIG. 9, it is assumed that the means for controlling the times of the transmitted pulses, the gain of the variable gain amplifier, the phase angle $\Omega_h(t)$ and the taps on the master delay lines are the same or equivalent to those shown in FIG. 7. Only one transducer channel is shown, but the others would be similar.

A transducer signal, $E_h(t)\cos(w_c t + \phi_h)$, provided by a transducer 106, is applied via a protection circuit 108 and a variable gain amplifier 110 to a mixer 112 where it is heterodyned with the same oscillator signal, $\cos(-w_o t + \Omega_h(t))$, as in FIG. 5C or in FIG. 7. The transducer signal is also applied to a mixer 114 wherein it is heterodyned with an oscillator signal $\sin(w_o t + \Omega_h(t))$. The latter oscillator signal can be derived from the former oscillator signal by inserting a delay 116 that is equal to one-quarter of a period of the frequency $w_o$.

The output of the mixer 112 is applied to a tap on an electrical master delay line 118 determined by a tap selector 120, and after passing through the delay line 118 and a low pass filter 121, it is heterodyned in a mixer 122 with a signal, $\cos w_1 t$. The output of the mixer 114 is applied to an identical tap on an identical electrical master delay line 124 determined by a tap selector 126, and after passing through the delay line 124 and a low pass filter 128 identical to low pass filter 121, it is heterodyned in a mixer 130 with a signal, $\sin w_1 t$. By choosing $w_o = w_c$, the delay lines and low pass filters require bandwidths only wide enough to pass the envelopes $E_h(t)$ of the signals supplied by the transducers. The outputs of the mixers 122 and 130 are applied to an adder 132. If $w_1 = w_o$, the outputs of the mixers 122 and 130 have the frequency $w_c$. Alternatively, signal processing can be done on the outputs of the low pass filters 121 and 128, rather than applying them to the mixers 122 and 130, e.g., by taking the square root of the sum of the squares of the mixer outputs. Digital signals could be used in all mixers. If desired, incremental lines of low cost can be inserted at the points x as was done in FIG. 7. Phase shifters can be inserted on either side of the mixers 112 and 114, as explained in connection with FIG. 8, thus permitting the use of an oscillator or clock having constant phase and deriving quadrature phases from it. The quadrature technique is especially suitable if delay lines 118 and 124 are implemented with charge-coupled devices (CCDs).

DOUBLE CONVERSION

Figure 10:
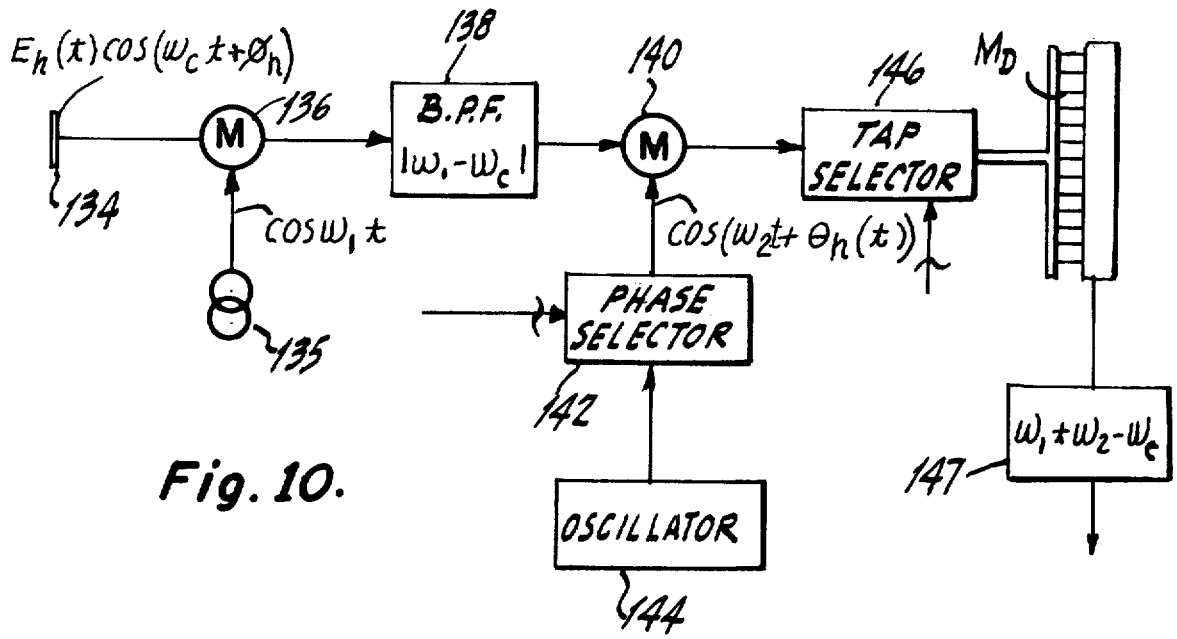
FIG. 10 illustrates a double heterodyning system.

FIG. 10 shows an implementation using double conversion. The signal $E_h(t)\cos(w_c t + \phi_h)$ supplied by a transducer 134 is heterodyned with the output $\cos w_1 t$ of an oscillator 135 in a mixer 136. The same oscillator output, i.e., the same phase, is applied to the corresponding mixers of all channels. A filter 138 selects the lower sideband ($w_1 - w_c$) from the output of the mixer 136 and applies it to the input of a mixer 140 wherein it is heterodyned with $\cos(w_2 t + \theta_h(t))$ selected by a phase selector 142 that is controlled in the same way as the phase selector 32 of FIG. 7 to select the output of an oscillator 144 of the desired phase. A tap selector 146 that is controlled in the same manner as the tap selector 38 of FIG. 7 connects the output of the mixer 140 to appropriate taps on the master delay line $M_D$. The output of the delay line $M_D$ is applied to a filter 147 that selects the upper sideband ($w_1 + w_2 - w_c$). Precise phase coherence is obtained if the delay provided at the tap is ideal, i.e., = $T_h(t)$, and if the phase angle $\theta_h$ satisfies the expression $$\theta_h(t - T_h(t)) = (w_1 + w_2) T_h(t) \quad (16)$$

wherein $(w_1 + w_2)$ is substituted for $w_o$ in expression (6).

In order to allow for more widely spaced taps in accordance with an aspect of this invention, the phase angle $\Omega_h(t)$ is substituted for $\theta_h(t)$ and may be determined by substituting $(w_1 + w_2)$ for $W_o$ in equation (13) or in equation (14). Equation (13) would become $$\Omega_h(t) = (w_1 + w_2) T_h^{} + w_c[T_h(t + T_h^{}) - T_h^{**}].$$

In order to reduce the number of taps to be selected, the outputs of the second mixers, like 140, of the channels for adjacent transducers can be added before application to tap selectors like 146. Although involving additional expense, the phase angle $\Omega_h(t)$ could be provided by phase shifters located at either the input or the output of the mixer 140, in which event the phase of the $w_2$ would be held constant, as discussed in connection with FIG. 8.

In FIG. 10, the lower sideband at the output of the mixer 136 and the upper sideband at the output of the mixer 140 are selected by the filters 138 and 147 respectively, but any combination of sidebands could be used as long as the appropriate value of $\Omega_h(t)$ is employed as set forth in the table below, in which Case #1 is that illustrated by FIG. 10. Each combination of $w_1$ and $w_2$ may be considered as an effective oscillator frequency and can be substituted for $w_o$ in the various equations.

| Case | S.B. from 136 | S.B. from 140 | $\Omega_h(t)$ |
|---|---|---|---|
| #1 | $w_1 - w_c$ | $w_2 + w_1 - w_c$ | $(w_2 + w_1)T_h^{} + w_c[T_h(t + T_h^{}) - T_h^{**}]$ |
| #2 | $w_1 - w_c$ | $w_2 - w_1 + w_c$ | $(w_2 - w_1)T_h^{} - w_c[T_h(t + T_h^{}) - T_h^{**}]$ |
| #3 | $w_1 + w_c$ | $w_2 - w_1 - w_c$ | $(w_2 - w_1)T_h^{} + w_c[T_h(t + T_h^{}) - T_h^{**}]$ |
| #4 | $w_1 + w_c$ | $w_2 + w_1 + w_c$ | $(w_2 + w_1)T_h^{} - w_c[T_h(t + T_h^{}) - T_h^{**}]$ |

Figure 11:
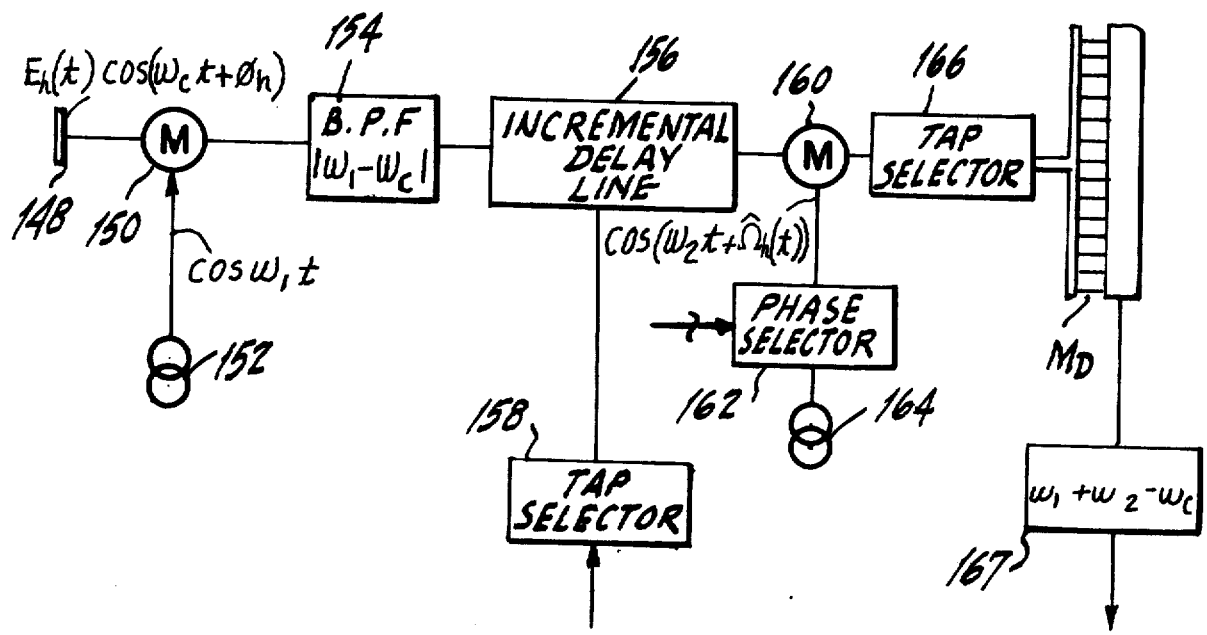
FIG. 11 illustrates a double heterodyning system incorporating an incremental delay line.

FIG. 11 shows a transducer channel having two mixers, one before and one after an incremental delay line so as to offer the ability to use different intermediate frequencies for a time varying incremental delay line and the master delay line having a fixed delay. Another advantage is that the "anticipation" required in the phase compensation, $\Omega_h(t)$, is simplified because the phase compensation occurs after the time-varying portion of the time delay rather than before it. A transducer 148 supplies a signal, $E_h(t)\cos(w_c t + \phi_h)$, to a mixer 150 wherein it is heterodyned with a constant phase of $\cos w_1 t$ from an oscillator 152 to produce intermediate frequencies, $(w_1 - w_c)$ and $(w_1 + w_c)$. The same phase of oscillator frequency is applied to the corresponding mixers of the other transducer channels. As in FIG. 10, the lower sideband ($w_1 - w_c$) of the resulting IF carrier wave is selected by a filter 154 that is connected between the output of the mixer 150 and one end of an incremental delay line 156 having a delay $T_{ih}(t)$. A tap selector 158 that may be operated as the tap selector 90 of FIG. 7 connects one of the taps of the incremental delay line 156 to a mixer 160 wherein it is heterodyned with the output $\cos w_2 t + \Omega_h(t)$ selected by a phase selector 162 from an oscillator 164 to produce an IF carrier and its sidebands. The frequency $w_2$ having the phase $\Omega_h(t)$ required in this situation can be provided by loading a ROM with the appropriate information and using it to control the phase selector 162 in the same way that the ROM 78 controls the tap selector 38 in FIG. 7. The output of the mixer 160 is connected to the input of a tap selector 166 that is controlled as the tap selector 38 of FIG. 7 to apply the IF waves to one of the taps of a master delay line $M_D$ having a delay $T_{MD}$. A filter 167 at the output of the delay line $M_D$ selects the upper sideband $(w_1+w_2-w_c)$ just as in FIG. 10.

If the tap on $M_D$ remains at the delay $T_{MD}$ during the focal scanning of a range along the radial direction, the incremental delay, $T_{ih}(t)$, of the line 156 must be as set forth in the following equation if the combined delays of the two lines is to equal the ideal delay $T_h(t)$.

$$T_{ih}(t) = T_h(t + T_{MD}) - T_{MD} \tag{18}$$

Because the incremental line has taps, it is unlikely that it will provide the ideal delay but rather a delay $T_{ih}^*$ of the tap closest to $T_{ih}(t)$ so that $$T_{ih}^*(t) = T_h^*(t + T_{MD}) - T_{MD}. \tag{19}$$

In this event, the phase angle $\Omega_n(t)$ of the frequency of the oscillator 164 that is coupled to the mixer 160 is $$\hat{\Omega}_h(t - T_{MD}) = w_1 T_h^*(t) + w_2 T_{MD} +$$
$$w_c[T_h(t) - T_h^*(t)]. \tag{20}$$

and substituting the expression $t+T_{MD}$ for the free variable t, we obtain $$\hat{\Omega}_h(t) = w_1 T_h^*(t+T_{MD}) + w_2 T_{MD} +$$
$$w_c[T_h(t+T_{MD}) - T_h^*(t+T_{MD})]. \tag{21}$$

A correction to the phase angle can be added to compensate for errors in location of the taps, as explained in connection with FIG. 7A.

It can be seen from equation (21) that the phase angle $\Omega_h(t)$ has components that compensate for the effect of injecting each oscillator frequency. These are determined by multiplying the frequency expressed in radians times the actual delay beyond the point of injection. The angle also includes a component determined by multiplying the carrier frequency in radians by the difference between the ideal delay required for a particular transducer and the actual delay in order to attain focussing. Regardless of the complexity of the heterodyning system employed, these two components must be provided. The actual phase angle used can, as previously explained, be the closest 45° or some other arbitrarily selected number of degrees. The point at which the phase adjustments are made does not matter as long as the resultant phase of the intermediate frequency carrier waves is within the arbitrarily selected limit at the input to the delay line system. Therefore, where two heterodyning means are used, the required total phase shift can be divided between them in any desired manner. Just as in FIG. 10, any combination of sidebands can be selected as long as the appropriate sign is used for the terms $$w_c[T_h(t + T_{MD}) - T_h^*(t + T_{MD})]$$

and $$w_1 T_h^*(t + T_{MD}).$$

SUMMARY

By controlling the phase of the waves derived from the transducers and applied to the inputs or taps of the delay means, whether they are carrier waves or intermediate frequency waves, in such manner that they arive at the summing point with sufficient phase coherence to form a useful video signal, it is possible to use delay means having fewer inputs or taps than would be required to produce the required phase coherence if the delay means alone were to be relied on, as in the prior art. This not only greatly reduces the cost of electrical delay lines if they are used and the reflection problems of acoustic lines if they are used, but it also can eliminate deleterious effects of noise produced by the tap switching required in prior equipment. By way of example, good results have been attained with an oscillator frequency of 4.5 MHz, a carrier frequency of 2.5 MHz, a pulse length of 1.5 us, an array such as illustrated in FIG. 6 that has an aperture of 2.2 cm and a 12 us master delay line having taps at every 0.5 us. From FIG. 6, it can be seen that this tap spacing is far too coarse to provide reasonable phase coherence of the intermediate frequency waves of 2 MHz at the summing point. In order to provide phase coherence within ±22.5°, the taps would have to be 50 ns apart rather than 500 ns, i.e., ten times as many would be required. Even coarse tap spacing could be used if less pulse overlap is satisfactory.

Whereas this invention facilitates dynamic focussing, it can reduce the cost of a fixed focus system by permitting the use of coarsely spaced delay line taps or it can enable a fixed focus system to operate at higher frequency with a given tap spacing.

In the embodiments of the invention described, the same array of transducers is used for transmitting pulses of acoustic energy into the body being examined and for receiving energy reflected from a given focal point, but inasmuch as the invention relates to the focussing of an array, two separate arrays that are oriented in any desired manner can be used. Alternatively, the energy may be introduced by sources that are not involved with the invented apparatus in any way, and the receiving array can be focussed in accordance with the invention.

What is claimed is:

1. In apparatus for forming images from energy contained in pulses of cycles of ultrasonic pressure waves that are transmitted into a body to be examined, the combination of an array of transducers, each transducer translating pressure waves impinging on it into corresponding electrical waves, a plurality of phase changing means, each having an input and an output, means respectively coupling the inputs of said phase changing means to receive the electrical waves provided by different transducers, delay means providing different discrete amounts of delay between each of a plurality of inputs and a summing point, means for respectively coupling the outputs of said phase changing means during a predetermined period to selected inputs of said delay means, said selected inputs having the discrete delays closest to the ideal compensating delays required for respectively focussing the transducers of the array at a given focal point, the differences between the said closest discrete delays and the ideal compensating delays being such that the pulses of electrical waves resulting from pressure waves reflected to the transducers from the given point arrive at said summing point at different times, and phase control means coupled to said phase changing means for causing the latter to set the phase of the waves at the outputs of each of said phase changing means so that the cycles of electrical waves within the portion of said pulses that arrive at said summing point in overlapped relationship have sufficient phase coherence at at least one time during said predetermined period to produce a signal having greater amplitude than any of the individual electrical waves.

2. The combination set forth in claim 1 wherein said means for controlling the phase of the waves at the output of each of said phase changing means sets the phases of the cycles of electrical waves at the outputs of said phase changing means so that they arrive at said summing point with precise phase coherence a plurality of times during said predetermined period.

3. The combination as set forth in claim 1 wherein each of said phase changing means is a phase shifter responsive to said phase control means.

4. The combination as set forth in claim 1 wherein each of said phase changing means includes
at least one mixer coupled between the input and output of said phase changing means,
a source of waves of a given frequency coupled to said mixer so as to cause it to produce electrical waves of upper and lower bands of intermediate frequency, and
means for setting the phase of the waves coupled from said source to said mixer in response to said phase contriol means.

5. The combination as set forth in claim 1 wherein each of said phase changing means includes
at least one mixer,
a phase shifter coupled in series with said mixer between the input of said phase changing means and its output,
a source of waves of a given frequency coupled to said mixer so as to cause it to produce waves of an intermediate frequency, and
means for setting the phase shift provided by said phase shifter in response to said phase control means.

6. In apparatus for forming real time images of portions of a body from signals derived from energy contained in pulses of ultrasonic pressure carrier frequency waves that are transmitted into the body, the combination of
an array of transducers, each of said transducers translating the pulses of ultrasonic carrier pressure waves impinging on them into corresponding pulses of electrical waves,
delay means having a plurality of input taps and a summing point,
a plurality of phase changing means, each having an input coupled to a different transducer and an output coupled to a tap on said delay means, each of said phase changing means producing electrical waves of a given frequency at its output,
the input taps on said delay means being spaced from said output so that the smallest difference in the delays between adjacent taps and said output is more than an eighth of a period of the electrical waves of the carrier frequency supplied to said phase changing means from the outputs of said transducers, and
means for causing each said phase changing means to set the phase of the waves of the given frequency that it produces in response to carrier waves reflected from a given focal point so that the waves of the given frequency arrive at said summing point of said delay means with a phase sufficiently close to the phases of waves of the given frequency arriving at said output from other phase changing means to produce a signal of relatively greater amplitude than the amplitude of the waves from each phase changing means.

7. In apparatus for deriving signals that can be used to form images of a body in response to energy contained in pulses of pressure waves, the combination of
means for repeatedly transmitting pulses of pressure waves of a frequency $w_c$ into a body,
an array of transducers,
a plurality of phase changing means, each having an input and an output, and including means for heterodyning signals applied to its input with an effective frequency $w_o$ so as to produce pulses of intermediate frequencies and also having means for controlling the phase $\Omega_h$ of the intermediate frequencies,
means respectively coupling the inputs of said phase changing means to different transducers,
delay means providing different discrete amounts of delay between each of a plurality of inputs and a summing point,
means coupling the outputs of said phase changing means during a predetermined period after the transmission of each pulse of pressure waves to selected inputs of said delay means, said selected inputs having delays $T_h^{}$ closest to the ideal compensating delays $T_h(t)$ required for focussing the array at a given focal point, the difference between the discrete delays $T_h^{}$ and the ideal delays $T_h$ being such that the pulses of intermediate frequency waves provided by a plurality of said phase changing means to the inputs of said delay means arrive at said summing point at different times, and
control means coupled to the phase control means in each phase changing means for causing the intermediate frequency waves at the output of the phase changing means to have at at least one time t during said period to a phase $\Omega_h$ comprised of a fixed component $w_o T_h^{}$ combined with a variable component $w_c[T_h(t + T_h^{}) - T_h^{**}]$ wherein $T_h(t)$ is the ideal compensating delay at time t.

8. In apparatus for deriving signals that can be used to form images of a body in response to energy contained in pulses of pressure waves, the combination of
means for repeatedly transmitting pulses of pressure waves of a frequency $w_c$ into a body,
an array of transducers for translating pressure waves that impinge on them into corresponding electrical waves,
a plurality of mixers, each having first and second inputs and an output, the first inputs of said plurality of mixers being respectively coupled to a plurality of said transducers,
means for respectively applying to said second inputs of said mixers selected phases $\Omega_h$ of a wave having a frequency $w_o$ so as to produce pulses of upper and lower sidebands of intermediate frequencies at the outputs of said mixers, a summing point, means respectively providing during a given period after the transmission of each pulse predetermined discrete delays between each of the outputs of said mixers and said summing point, the discrete delays being those closest to the ideal compensating delays required for focussing the transducers at a given focal point, the respective differences between the discrete delays and the ideal compensating delays being such that the pulses of intermediate frequencies at the outputs of the mixers arrive at said summing pointr at different times, and means for making the selected phases of the waves of the frequency $w_o$ that are applied to said second inputs of said mixers respectively have at at least one time during said given period a fixed component equal to $w_o$ times the delay between the output of the mixer and said summing point and a variable component equal to the frequency $w_c$ times the difference between the discrete delay between the output of the mixer and said summing point and the ideal compensating delay required to focus the transducers.

9. In apparatus for deriving signals that can be used to form images of a body in response to energy contained in pulses of pressure waves, the combination of means for repeatedly transmitting pulses of pressure waves of a frequency $w_c$ into a body, an array of transducers for translating pressure waves that impinge on them into corresponding electrical waves, a plurality of mixers, each having first and second inputs and an output, the first inputs of said plurality of mixers being respectively coupled to a plurality of said transducers, means for respectively applying to said second inputs of said mixers selected phases $\Omega_h$ of a wave having a frequency $w_o$ so as to produce pulses of upper and lower sidebands of intermediate frequencies at the outputs of said mixers, a summing point, means respectively providing during a given period after the transmission of each pressure pulse discrete delays $T_h^{}$ between each of the outputs of said mixers and said summing point that are respectively closest to the ideal compensating delays $T_h(t)$ required for focussing the array at a given focal point, the differences between $T_h^{}$ and $T_h(t)$ being such that the pulses of intermediate frequency waves at the outputs of said mixers that are related to pulses of pressure waves reflected from said given focal point arrive at said summing point at different times, said means for applying selected phases of a frequency $w_o$ being such as to cause the phase $\Omega_h$ of intermediate frequency waves at the outputs of said mixers at at least one time t during said period to have a fixed component within a predetermined number of radians of $w_o T_h^{}$ and a variable component within a predetermined number of radians of $w_c[T_h(t + T_h^{}) - T_h^{**}]$ wherein $T_h(t)$ is the expression for the ideal compensating delay as a function of time.

10. The combination as set forth in claim 9 wherein means are coupled to said summing point for forming images from the signals appearing thereat, and filter means for passing only one of said sidebands of intermediate frequencies coupled between the outputs of said mixers and said latter means.

11. The combination as set forth in claim 10 wherein said fixed and variable components of the phase $\Omega_h$ are both positive and wherein the sideband of intermediate frequencies passed by said filter means is the lower sideband.

12. The combination as set forth in claim 10 wherein said fixed component of said phase $\Omega_h$ is positive and said variable component is negative and wherein the sideband of intermediate frequencies passed by said filter means is the upper sideband.

13. In apparatus for forming real time images of portions of a body from signals derived from energy contained in pulses of ultrasonic pressure carrier frequency waves of a given duration that are transmitted into the body, the combination of an array of transducers, each of said transducers translating the pulses of ultrasonic carrier pressure waves impinging on them into corresponding pulses of electrical waves, delay means having a plurality of input taps and an output, a plurality of phase changing means, each having an input coupled to a different transducer and responsive to a pulse of electrical waves supplied by that transducer to provide at an output thereof a pulse of electrical waves having a selected phase, tap selecting means for respectively connecting the outputs of said phase changing means to selected taps on said delay means, and means for focussing the array at a point along a given direction comprising control means coupled to each of said phase changing means for causing it to set the selected phase of the electrical waves at its output that are related to reflected pressure waves received at the transducer from the given point at such an angle that they arrive at the output of said delay line means with sufficient phase coherence to provide a greater signal than would result from electrical waves having random phase relationships.

14. Apparatus as described in claim 13 wherein means are provided for making said control means cause the phase changing means to set the selected phase of the electrical waves at successively different locations so that the waves at its output that are related to pressure waves reflected from a series of points and received at the transducer arrive at the output of said delay line with precise phase coherence.

15. Apparatus as described in claim 13 wherein each of said phase changing means is comprised of a phase shifter.

16. Apparatus as set forth in claim 13 wherein said phase changing means includes a mixer having first and second inputs and an output, a phase shifter connected between the transducer and said first input, the angle by which said phase shifter shifts the signals applied to it being determined by connection to said control means, a source of electrical waves, said source being coupled to said second input of said mixer, and said output of said mixer being connected to said tap selecting means.

17. Apparatus as set forth in claim 13 wherein said phase changing means for changing the phase of the alternating current electrical waves includes a mixer having first and second inputs and an output, a phase shifter connected between the output of said mixer and said tap selecting means, the angle by which said phase shifter shifts the signals applied to it being determined by connection to said control means, and a source of waves having a frequency different from said carrier frequency, said source being coupled to said second input of said mixer.

18. Apparatus as set forth in claim 13 wherein each means for changing the phase of the alternating current electrical waves includes a mixer having first and second inputs and an output, said first input of said mixer being coupled to the transducer, a source for respectively supplying at outputs thereof different phases of waves having a given frequency, means for selectively coupling one of said outputs to said second input of said mixer, the output selected being determined by connection to said control means, whereby pulses of intermediate frequency waves of the selected phase appear at the outputs of said mixers.

19. Apparatus as described in claim 18 wherein the means for supplying different phases of a frequency different from that of said carrier waves includes a digital clock and digital means for selecting one of several output phases thereof and applying it to said second input of said mixer.

20. Apparatus as described in claim 18 wherein the frequency supplied by said source is such that the frequency of said intermediate frequency waves is lower than the frequency of the carrier waves.

21. Apparatus as described in claim 18 wherein the frequency supplied by said source is such that the frequency of said intermediate frequency waves is higher than the frequency of said carrier waves.

22. Apparatus as described in claim 18 wherein the frequency supplied by said source is such that the frequency of said intermediate frequency is the same as the frequency of the carrier waves.

23. Apparatus as described in claim 21 wherein said delay line means is an acoustic delay line.

24. Apparatus as set forth in claim 23 wherein means are provided for changing the phase of the intermediate frequency waves applied to each tap by an amount such as to compensate for any error in the delay provided by the tap.

25. In an ultrasonic scanner for producing real time images of the human body from carrier presusre waves comprising, an array of transducers for converting pulses of alternating carrier pressure waves into corresponding pulses of alternating current electrical waves, the difference in compensating delay required by at least some of said transducers when they are focussed over a given range along a given direction being greater than one-eighth a period of the carrier pressure waves, phase changing means coupled to each transducer, delay line means having a plurality of input taps and an output, the delays between said taps and said output differing by more than one-eighth of the period of the carrier pressure waves, means for connecting the output of each of said phase changing means to a tap on said delay lines means during the time reflections are received from targets within said given range, and means for focussing said array between minimum and maximum points of said range comprising means for causing at least some of said phase changing means to change the phase of the electrical waves they provide in such manner that they arrive at the output of said delay line means within less than 180° of each other.

26. In a system for producing real time images of a body from pulses of ultrasonic carrier pressure waves, the combination of a transducer, first and second heterodyning means having inputs coupled to the output of said transducer, said heterodyning means providing at their respective outputs bands of intermediate frequencies having phase quadrature relationships, a first delay line means having a plurality of input taps and an output, means for connecting the output of said first heterodyning means to an input tap on said first delay line means, a second delay line means having a plurality of input taps and an output, means for connecting the output of said second heterodyning means to an input tap on said second delay line means, and a summing point coupled to said outputs of said delay lines.

27. The combination as set forth in claim 26 wherein there is also included a first mixer having two inputs and an output, one of said inputs being coupled to the output of said first delay line means, said output of said mixer being connected to said summing point, and a second mixer having two inputs and an output, one of said inputs being coupled to the output of said second delay line means, said output of said mixer being connected to said summing point, and means for respectively applying waves having phase quadrature relationship to the other inputs of said first and second mixers.

28. In apparatus for producing real time images of a portion of a body from pulses of ultrasonic carrier waves, $E_h(t) \cos(w_c t + \phi_h)$, the combination of a transducer, a source of wave $\cos w_1 t$, a first mixer having first and second inputs and an output, said first input being connected to said transducer, said second input being connected to said source, a second mixer having first and second inputs and an output, a band pass filter passing frequencies $(w_1 - w_c)$ connected between said output of said first mixer and said first input of said second mixer, delay line means having a plurality of input taps, means for connecting the output of said second mixer to one of said taps, and a source of waves $\cos[w_2 + \Omega_h(t)]$ coupled to said second input of said second mixer, wherein $$\Omega_h(t) = (w_1 + w_2)T_h^{} + w_c[T_h(t + T_h^{}) - T_h^{**}],$$

modulo $2\pi$ radians, in which $T_h^{**}$ is the delay at the tap to which the transducer is connected and $T_h(t)$ is the ideal delay for that transducer.

29. In apparatus for producing real time images of a portion of a body from pulses of ultrasonic carrier waves, $E_h(t) \cos(w_c t + \phi_h)$, the combination of a transducer, a source of wave $\cos w_1 t$, a first mixer having first and second inputs and an output, said first input being connected to said transducer, said second input being connected to said source, a second mixer having first and second inputs and an output, a band pass filter passing frequencies $(w_1 - w_c)$ connected between said output of said first mixer and said first input of said second mixer, delay line means having a plurality of input taps, means for connecting the output of said second mixer to one of said taps, and a source of waves $\cos [w_2 + \Omega_h(t)]$ coupled to said second input of said second mixer, wherein $$\Omega_h(t) = (w_2 - w_1)T_h^{} - w_c[T_h(t + T_h^{}) - T_h^{**}],$$

modulo $2\pi$ radians, in which $T_h^{**}$ is the delay at the tap to which the transducer is connected and $T_h(t)$ is the ideal delay for that transducer.

30. In apparatus for producing real time images of a portion of a body from pulses of ultrasonic carrier waves, $E_h(t) \cos (w_c t + \phi_h)$, the combination of a transducer, a source of wave $\cos w_1 t$, a first mixer having first and second inputs and an output, said first input being connected to said transducer, said second input being connected to said source, a second mixer having first and second inputs and an output, a band pass filter passing frequencies $(w_1 + w_c)$ connected between said output of said first mixer and said first input of said second mixer, delay line means having a plurality of input taps, means for connecting the output of said second mixer to one of said taps, and a source of waves $\cos [w_2 + \Omega_h(t)]$ coupled to said second input of said second mixer, wherein $$\Omega_h(t) = (w_2 - w_1)T_h^{} + w_c[T_h(t + T_h^{}) - T_h^{**}],$$

modulo $2\pi$ radians, in which $T_h^{**}$ is the delay at the tap to which the transducer is connected and $T_h(t)$ is the ideal delay for that transducer.

31. In apparatus for producing real time images of a portion of a body from pulses of ultrasonic carrier waves, $E_h(t) \cos (w_c t + \phi_h)$, the combination of a transducer, a source of wave $\cos w_1 t$, a first mixer having first and second inputs and an output, said first input being connected to said transducer, said second input being connected to said source, a second mixer having first and second inputs and an output, a band pass filter passing frequencies $(w_1 + w_c)$ connected between said output of said first mixer and said first input of said second mixer, delay line means having a plurality of input taps, means for connecting the output of said second mixer to one of said taps, and a source of waves $\cos [w_2 + \Omega_h(t)]$ coupled to said second input of said second mixer, wherein $$\Omega_h(t) = (w_2 + w_1)T_h^{} - w_c[T_h(t + T_h^{}) - T_h^{**}],$$

modulo $2\pi$ radians, in which $T_h^{**}$ is the delay at the tap to which the transducer is connected and $T_h(t)$ is the ideal delay for that transducer.

32. In apparatus for producing real time images of a portion of the body from pulses of ultrasonic carrier waves, $E_h(t) \cos (w_c t + \phi_h)$, the combination of a transducer, a source of waves $\cos w_1 t$, a first mixer having first and second inputs and an output, said first input being connected to said transducer and said second input being connected to said source, a second mixer having first and second inputs and an output, a band pass filter passing the frequencies $(w_1 - w_c)$ and an incremental delay line connected in series between the output of said first mixer and said first input of said second mixer, means for selecting the delay supplied by said incremental delay line, a master delay line having a plurality of input taps, means for connecting the output of said second mixer to one of said input taps, and a source of waves $\cos (w_2 t + \Omega_h(t))$ coupled to said second input of said second mixer, wherein $$\Omega_h(t) = w_1 T_h^*(t + T_{MD}) + w_2 T_{MD} + w_c[T_h(t + T_{MD}) - T_h^*(t + T_{MD})],$$

and in which $T_h^*$ = the actual delay from the tap of the incremental delay line to the output of the master delay line, and $T_h(t)$ is the ideal compensating delay for the transducer.

33. In apparatus for forming real time images of portions of a body from signals derived from pulses of ultrasonic pressure carrier frequency waves $w_c$ transmitted into the body comprising an array of transducers, a plurality of mixers, each mixer having first and second inputs and an output, circuits respectively coupling said transducers to said first inputs of said mixers, a source of different phases of alternating current waves having a frequency $w_o$, phase selectors for respectively applying at selected times a phase $\Omega_h(t)$ of the alternating current waves from said source to said second inputs of said mixers so as to produce upper and lower sidebands at the outputs thereof, the phase $\Omega_h(t)$ being varied with time so as to be within a predetermined number of degrees of the angle specified by the expression $$w_o T_h^{} + w_c[T_h(t + T_h^{}) - T_h^{**}]$$

wherein h is the distance from the transducer to the center line of the array, $T_h^{**}$ is the actual delay between the tap to which a transducer is coupled via its associated mixer and the output of the master delay line and $T_h(t)$ is the ideal compensating delay that would produce precise phase coherence, a master delay line having a plurality of input taps and an output, coupling circuits for respectively applying the outputs of said mixers to selected input taps on said master delay line, an output terminal coupled to said output of said delay line, and filtering means for premitting only the lower sideband to pass to said output terminal.

34. In apparatus for forming real time images of portions of a body from signals derived from pulses of ultrasonic pressure carrier frequency waves $w_c$ transmitted into the body comprising an array of transducers, a plurality of mixers, each mixer having first and second inputs and an output, circuits respectively coupling said transducers to said first inputs of said mixers, a source of different phases of alternating current waves having a frequency $w_o$, phase selectors for respectively applying at selected times a phase $\Omega_h(t)$ of the alternating current waves from said source to said second inputs of said mixers so as to produce upper and lower sidebands at the outputs thereof, the phase $\Omega_h(t)$ being varied with time so as to be within a predetermined number of degrees of the angle specified by the expression $$w_o T_h^{} - w_c[T_h(t + T_h^{}) - T_h^{**}]$$

wherein h is the distance from the transducer to the center line of the array, $T_h^{**}$ is the actual delay between the tap to which a transducer is coupled via its associated mixer and the output of the master delay line, and $T_h(t)$ is the ideal compensating delay that would produce precise phase coherence, a master delay line having a plurality of input taps and an output, coupling circuits for respectively applying the outputs of said mixers to selected input taps on said master delay line, an output terminal coupled to said output of said delay line, and filtering means for permitting only the upper sideband to pass to said output terminal.

35. In an ultrasonic scanner for producing images from carrier pressure waves a plurality of transducers for converting pressure waves into corresponding electrical waves, first phase changing means coupled to each of said transducers, delay line means having a plurality of taps and an output, said taps having errors in their respective spacing from said output, second phase changing means respectively coupled between the outputs of said first phase changing means and each of said taps, said second phase changing means adjusting the phase of signals applied to it so as to compensate for errors in the spacing of said taps, and means for applying the output of each phase changing means to a desired input circuit.

36. An ultrasonic scanner as set forth in claim 35 wherein said second phase changing means includes a plurality of mixers, each having first and second inputs and an output, one input of each mixer being respectively coupled to the output of one of said first phase changing means, and means for providing a frequency $w_1$ of a given phase to the other input of said mixer, the frequency $w_1$ being such as to produce bands of frequencies being within the pass band of said delay line, the given phase having a first component compensating for errors in the spacing of the tap to which the output of the mixer is connected and a second component equal to $w_1 T_h^{}$, wherein $T_h^{}$ is the delay provided by the tap to which the output of the mixer is connected.

* * * * *